(12) United States Patent
Keim et al.

(10) Patent No.: US 9,340,836 B2
(45) Date of Patent: May 17, 2016

(54) ALLELIC DISCRIMINATION ASSAYS FOR MRSA STRAINS

(75) Inventors: Paul Keim, Flagstaff, AZ (US);
Elizabeth Driebe, Flagstaff, AZ (US);
David Engelthaler, Flagstaff, AZ (US);
Jolene Bowers, Flagstaff, AZ (US)

(73) Assignees: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 910 days.

(21) Appl. No.: 13/607,416

(22) Filed: Sep. 7, 2012

(65) Prior Publication Data
US 2015/0259727 A1    Sep. 17, 2015

Related U.S. Application Data

(60) Provisional application No. 61/531,729, filed on Sep. 7, 2011.

(51) Int. Cl.
*C12Q 1/68*    (2006.01)

(52) U.S. Cl.
CPC .......... *C12Q 1/689* (2013.01); *C12Q 2600/118* (2013.01); *C12Q 2600/156* (2013.01); *C12Q 2600/16* (2013.01)

(58) Field of Classification Search
None
See application file for complete search history.

(56) References Cited

PUBLICATIONS

Moser et al. Multiple-locus variable-number tandem-repeat analysis of meticillin-resistant *Staphylococcus aureus* discriminates within USA pulsed-field gel electrophoresis types. Journal of Hospital Infection 71:333-339 (2009).*
Kuroda et al. Whole genome sequencing of meticillin-resistant *Staphylococcus aureus*. The Lancet 357:1225-1240 (2001).*
Diep et al. Complete genome sequence of USA300, an epidemic clone of community-acquired meticillin-resistant *Staphylococcus aureus*. The Lancet 367:731-739 (2006).*
Carroll et al. Draft genome sequence of strain CBD-635, a methicillin-resistant *Staphylococcus aureus* USA100 isolate. GenomeA 1(4) e00491-13 (2013).*
Bei Resources Product Information Sheet for NR-45898 (2014).*
Stegger et al. Genome sequence of *Staphylococcus aureus* strain CA-347, a USA600 methicillin-resistant isolate. GenomeA 1(4) e00517-13 (2013).*

* cited by examiner

*Primary Examiner* — Samuel Woolwine

(57) ABSTRACT

The present invention provides assays, methods and kits that may be used to detect and differentiate MRSA isolates, e.g., USA100, USA300 and USA600 strains.

15 Claims, No Drawings

ALLELIC DISCRIMINATION ASSAYS FOR MRSA STRAINS

CROSS REFERENCE

This application is related to and claims the priority benefit of U.S. provisional application 61/531,729, filed on Sep. 7, 2011, the teachings and content of which are incorporated by reference herein.

STATEMENT REGARDING FEDERALLY SPONSORED RESEARCH

This invention was made with government support under AI066581 awarded by the National Institutes of Health. The government has certain rights in this invention.

FIELD OF THE INVENTION

The present invention generally provides compositions and methods to detect and differentiate methicillin-resistant *Staphylococcus aureus* (MRSA) USA100, USA300, and USA600 strains. More particularly, the present invention provides assays based on identified SNPs, primers and probes, designed accordingly, to detect the presence of specific MRSA strains.

BACKGROUND OF THE INVENTION

Methicillin-resistant *Staphylococcus aureus* (MRSA) has become one of the most dangerous infectious agents in the U.S. and elsewhere, with a higher mortality rate than HIV-AIDS. MRSA is a strain of *Staphylococcus aureus* (*S. aureus*) bacteria, a common type of bacteria that may live on the skin and in the nasal passages of healthy people. MRSA does not respond to some of the antibiotics generally used to treat *staphylococcus* and other bacterial infections.

Healthcare-associated MRSA (HA-MRSA) infections occur in people who are or have recently been in a hospital or other health-care facility. Many people may be at risk of MRSA infection due to receiving healthcare services in an environment where the MRSA bacteria are colonized on surfaces, healthcare workers, inpatients or outpatients. Community-associated MRSA (CA-MRSA) infections occur in otherwise healthy people who have not recently been in the hospital. In fact, MRSA has become a primary cause of skin and soft tissue infections among persons without extensive exposure to healthcare settings, and the outbreaks have occurred in athletic team facilities, correctional facilities, and military basic training camps.

Pulsed-field gel electrophoresis (PFGE) is a molecular method for typing MRSA. It is used to identify index strain(s) of an outbreak or understand the clonal relationship among strains. The nonlimiting PFGE reference strains include USA100, USA200, USA300, USA400, USA500, USA600, USA700, USA800, USA1100 (see Network on Antimicrobial resistance in *S. aureus* (NARSA), available at UTL: narsa.net/). However, many isolates of MRSA are indistinguishable when compared using the standard PFGE typing method. This may present a problem when investigating local outbreaks of MRSA transmission in a healthcare setting.

Strains that are identified as belonging to the USA100, USA300, and USA600 strain types have specific clinical relevance. USA100 type strains are more likely to be HA-MRSA strains, typically have increased multi-drug resistance, and are not thought to be as virulent as USA300 type strains. USA300 type strains are more likely to be CA-MRSA, are less multi-drug resistant than USA100 strains, and typically have increased virulence. USA600 has been found to be associated with a higher than average mortality rate for MRSA, especially when associated with bloodstream infections.

Microbiological identification systems are based on different analytical techniques, such as phenotypic, genotypic, and strain typing. Each system has limitations due to method and/or database limitations and shortcomings in terms of accuracy, reproducibility, technical complexity, speed, and cost. Considering these limitations and the level of identification required as to genus, species, and strain, there is an ongoing need for strain typing technology to link cases together and identify sources of infection using more rapid and informative tests with a high level of accuracy. With such an invention, it would be possible to rapidly identify individuals who are colonized with MRSA, and thus interventions for MRSA colonization through decolonization, isolation procedures, or restrictions in occupational activities among clinicians and patients would be more effective.

SUMMARY OF THE INVENTION

One aspect of the present invention provides a composition for identifying and differentiating MRSA strains in a sample, which comprises one or more strain specific primer sets, wherein each primer set comprises a first and a second isolated oligonucleotide, each comprising a sequence selected from the group consisting of SEQ ID NO. 9, SEQ ID NO. 10, SEQ ID NO. 13, SEQ ID NO. 14, SEQ ID NO. 17, SEQ ID NO. 18, SEQ ID NO. 21, and SEQ ID NO. 22 to a reaction mixture comprising the sample; and wherein the first isolated oligonucleotide is different from the second isolated oligonucleotide. Specifically, one strain specific primer set may comprise two oligonucleotides comprising SEQ ID NO. 9 and SEQ ID NO. 10, respectively; one strain specific primer set may comprise two oligonucleotides comprising SEQ ID NO. 13 and SEQ ID NO. 14, respectively; one strain specific primer set may comprise two oligonucleotides comprising SEQ ID NO. 17 and SEQ ID NO. 18, respectively; or one strain specific primer set may comprise two oligonucleotides comprising SEQ ID NO. 21 and SEQ ID NO. 22, respectively.

The primer set of the above general composition may further comprise a third and a fourth isolated oligonucleotide as probes corresponding to each strain specific primer set added, and the third or fourth oligonucleotide comprises a sequence selected from the group consisting of SEQ ID NO. 11, SEQ ID NO. 12, SEQ ID NO. 15, SEQ ID NO. 16, SEQ ID NO. 19, SEQ ID NO. 20, SEQ ID NO. 23, and SEQ ID NO. 24 to the reaction mixture comprising the sample. Said third isolated oligonucleotide is different from said fourth isolated oligonucleotide. Further, the third oligonucleotide comprises a first label, and the fourth oligonucleotide comprises a second label that is different from the first label. Specifically, the third and fourth oligonucleotides corresponding to the strain specific primer set comprising two oligonucleotides comprising SEQ ID NO. 9 and SEQ ID NO. 10 are: an oligonucleotide comprising SEQ ID NO. 11 and an oligonucleotide comprising SEQ ID NO. 12; the third and fourth oligonucleotides corresponding to the strain specific primer set comprising two oligonucleotides comprising SEQ ID NO. 13 and SEQ ID NO. 14 are an oligonucleotide comprising SEQ ID NO. 15 and an oligonucleotide comprising SEQ ID NO. 16; the third and fourth oligonucleotides corresponding to the strain specific primer set comprising two oligonucleotides comprising SEQ ID NO. 17 and SEQ ID NO. 18 are an oligonucleotide comprising SEQ ID NO. 19 and an oligonucleotide comprising SEQ ID NO. 20; and the third and fourth oligonucleotides corresponding to the strain specific primer set comprising two oligonucleotides comprising SEQ ID NO. 21 and SEQ ID NO. 22 are an oligonucleotide comprising SEQ ID NO. 23 and an oligonucleotide comprising SEQ ID NO. 24.

Another aspect of the present invention provides a method of identifying and differentiating MRSA isolates in a sample, and the method comprises the steps of (1) receiving the sample; (2) adding one or more strain specific primer set(s), wherein each primer set comprises a first and a second isolated oligonucleotide, each comprising a sequence selected from the group consisting of SEQ ID NO. 9, SEQ ID NO. 10, SEQ ID NO. 13, SEQ ID NO. 14, SEQ ID NO. 17, SEQ ID NO. 18, SEQ ID NO. 21, and SEQ ID NO. 22, to a reaction mixture comprising the sample, wherein the first isolated oligonulceotide is different from the second isolated oligonulceotide; (3) subjecting the mixture to conditions that allow nucleic acid amplification; and (4) obtaining an allelic identification of amplification products that signifies the sample as containing MRSA USA100, USA300, USA600, non-MRSA USA100, USA300, or USA600 strains. The allelic identification or differentiation could be obtained on the basis of a comparison of the sequence of an unknown strain with the sequences indicative of each respective MRSA strain.

Preferably, one of the strain specific primer sets in the method comprises two oligonucleotides comprising SEQ ID NO. 9 and SEQ ID NO. 10, respectively.

Preferably, one of the strain specific primer sets in the method comprises two oligonucleotides comprising SEQ ID NO. 13 and SEQ ID NO. 14, respectively.

Preferably, one of the strain specific primer sets in the method comprises two oligonucleotides comprising SEQ ID NO. 17 and SEQ ID NO. 18, respectively.

Preferably, one of the strain specific primer sets in the method comprises two oligonucleotides comprising SEQ ID NO. 21 and SEQ ID NO. 22, respectively.

In further exemplification, when said method comprises adding the first oligonucleotide represented by SEQ ID NO. 9 and a second oligonucleotide represented by SEQ ID NO. 10, it may further comprise adding third and fourth oligonucleotide represented by SEQ ID NO. 11 and SEQ ID NO. 12, respectively, to the mixture; wherein said third oligonucleotide comprises a first label, wherein said fourth oligonucleotide comprises a second label that is different from said first label; and wherein the step of obtaining an allelic identification of amplification products in said method further comprises the step of collecting signals from the first and the second labels.

When said method comprises adding the first oligonucleotide represented by SEQ ID NO. 13 and a second oligonucleotide represented by SEQ ID NO. 14, it may further comprise adding a third and a fourth oligonucleotide represented by SEQ ID NO. 15 and SEQ ID NO. 16, respectively, to the mixture; wherein said third oligonucleotide comprises a first label, and said fourth oligonucleotide comprises a second label that is different from said first label; and wherein the step of obtaining an allelic identification of amplification products in said method further comprises the step of collecting signals from the first and the second labels.

When said method comprises adding the first oligonucleotide represented by SEQ ID NO. 17 and a second oligonucleotide represented by SEQ ID NO. 18, it may further comprise adding a third and a fourth oligonucleotide represented by SEQ ID NO. 19 and SEQ ID NO. 20, respectively, to the mixture; wherein said third oligonucleotide comprises a first label, and said fourth oligonucleotide comprises a second label that is different from said first label; and wherein the step of obtaining an allelic identification of amplification products in said method further comprises the step of collecting signals from the first and the second labels.

When said method comprises adding the first oligonucleotide represented by SEQ ID NO. 21 and a second oligonucleotide represented by SEQ ID NO. 22, it may further comprise adding third and fourth oligonucleotides represented by SEQ ID NO. 23 and SEQ ID NO. 24, respectively, to the mixture; wherein said third oligonucleotide comprises a first label, and said fourth oligonucleotide comprises a second label that is different from said first label; and wherein the step of obtaining an allelic identification of amplification products in said method further comprises the step of collecting signals from the first and the second labels.

Preferably, to obtain an allelic identification of amplification products, said method further comprises the step of collecting signals from the first and the second labels.

In further exemplification, to obtain an allelic identification of amplification products, said method further comprises the step of sequencing the amplification products.

Further, the allelic identifications in said method comprise: an USA300 allele identification represented by SEQ ID NO. 1; a non-USA300 allele identification represented by SEQ ID NO. 2; an USA300 allele identification represented by SEQ ID NO. 3; a non-USA300 allele identification represented by SEQ ID NO. 4; an USA600 allele identification represented by SEQ ID NO. 5; a non-USA600 allele identification represented by SEQ ID NO. 6; an USA100 allele identification represented by SEQ ID NO. 7; and a non-USA100 allele identification represented by SEQ ID NO. 8.

Yet another aspect of the present invention provides a A kit used to identify and differentiate MRSA strains in a sample, and the kit comprises: one or more strain specific primer sets, wherein each primer set comprises a first and a second isolated oligonucleotide, each comprising a sequence selected from the group consisting of SEQ ID NO. 9, SEQ ID NO. 10, SEQ ID NO. 13, SEQ ID NO. 14, SEQ ID NO. 17, SEQ ID NO. 18, SEQ ID NO. 21, and SEQ ID NO. 22 to a reaction mixture comprising the sample, wherein the first isolated oligonucleotide is different from the second isolated oligonucleotide; and an indication of a result that signifies an allelic identification of amplification products that indicates the sample as containing MRSA USA100, USA300, USA600, non-MRSA USA100, USA300, or USA600 strains.

Preferably, one of the strain specific primer sets in the kit comprises two oligonucleotides comprising SEQ ID NO. 9 and SEQ ID NO. 10, respectively. Such primer set may further comprise a third and a fourth oligonucleotides represented by SEQ ID NO. 11 and SEQ ID NO. 12, respectively; wherein the third oligonucleotide comprises a first label, and the fourth oligonucleotide comprises a second label that is different from the first label.

Preferably, one of the strain specific primer sets in the kit comprises two oligonucleotides comprising SEQ ID NO. 13 and SEQ ID NO. 14, respectively. Such primer set may further comprise a third and a fourth oligonucleotides represented by SEQ ID NO. 15 and SEQ ID NO. 16, respectively; wherein the third oligonucleotide comprises a first label, and the fourth oligonucleotide comprises a second label that is different from the first label.

Preferably, one of the strain specific primer sets in the kit comprises two oligonucleotides comprising SEQ ID NO. 17 and SEQ ID NO. 18, respectively. Such primer set may further comprise a third and a fourth oligonucleotides represented by SEQ ID NO. 19 and SEQ ID NO. 20, respectively;

wherein the third oligonucleotide comprises a first label, and the fourth oligonucleotide comprises a second label that is different from the first label.

Preferably, one of the strain specific primer sets in the kit comprises two oligonucleotides comprising SEQ ID NO. 21 and SEQ ID NO. 22, respectively. Such primer set may further comprise a third and a fourth oligonucleotides represented by SEQ ID NO. 23 and SEQ ID NO. 24, respectively; wherein the third oligonucleotide comprises a first label, and the fourth oligonucleotide comprises a second label that is different from the first label.

Further, the indication of a result of the kit is in a form selected from the group consisting of (1) ΔCt values for an amplification of an USA600 strain, an USA300 strain, an USA100 strain, a non-USA600 strain, a non-USA300 strain and a non-USA-100 strain, and (2) a nucleic acid sequence including a sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7 and SEQ ID NO. 8; wherein the sample containing a MRSA USA300 strain is signified by amplification products having an allelic identification comprising SEQ ID NO. 1 or SEQ ID NO. 3; or wherein the sample containing a MRSA non-USA300 strain is signified by amplification products having an allelic identification comprising SEQ ID NO. 2 or SEQ ID NO. 4.

Other aspects and iterations of the invention are described in more detail below.

DETAILED DESCRIPTION OF THE INVENTION

This disclosure provides genetic signatures specific to major strain types of MRSA (methicillin-resistant *Staphylococcus aureus*). A real-time Polymerase Chain Reaction (PCR) format, providing a straightforward, highly sensitive, specific assay system for rapidly typing strains is provided based on the signatures disclosed herein. The present invention discloses assays, methods and kits designed to identify and differentiate among USA100, USA300 and USA600 MRSA strains, which are considered clinically important.

(I) Detection of MRSA Strains (a) Molecules Identifying and Differentiating MRSA Strains The resistance of *Staphylococcus aureus* to b-lactam antibiotics is associated with the expression of penicillin-binding protein 2a (PBP2a). This protein is encoded by the mecA gene, which is situated on a mobile genetic element, staphylococcal cassette chromosome mec (SCCmec). Five different SCCmec types have been identified in methicillin-resistant *S. aureus* (MRSA) strains. SCCmec types I, II and III are mainly found in hospital-acquired MSRA (HA-MRSA), whereas SCCmec types IV and V are mainly associated with community-acquired MRSA (CA-MRSA). SCCmec contains the mec complex (mecA and its regulators) and the ccr gene complex, which encodes site-specific recombinases, responsible for the mobility of SCCmec.

*S. aureus* can produce a number of virulence factors. Panton-Valentine leucocidin (PVL) is predominantly associated with severe skin infections and necrotizing pneumonia. Toxic shock syndrome toxin-1 (TSST-1) is a 29.1 kDa super-antigen that is encoded by the tst gene. The release of TSST-1 into the bloodstream may give rise to a variety of severe clinical conditions, like toxic shock syndrome (TSS). PVL, together with SCCmec type IV, is suggested to be a marker for CA-MRSA, although there are exceptions. Among the PFGE types (USA100, USA200, USA300, USA400, USA500, USA600, USA700, and USA800), for example, the PFGE typing of USA100 is PVL (−)/TSST (−)/SCCmec II (staphylococcal cassette chromosome mec type II), PFGE typing of USA300 is PVL (+)/TSST (−)/SCCmec IV or PVL (−)/TSST (−)/SCCmec IV, and PFGE typing of USA600 is PVL(−)/TSST(−)/SCCmec II.

(i) Species or Strain Specific Nucleic Acid Sequences

Species or strain specific sequences are sequences unique to the species or strain, that is, not shared by other previously characterized species or strains. Oligonucleotides, such as a probe or primer, containing a sequence complementary to a sequence specific to a *S. aureus* strain will typically not hybridize to the corresponding portion of the genome of other species or strains under similar stringent conditions. The concept of oligonucleotides includes any DNA or RNA molecule of two or more nucleotides, whether from a natural source, chemically synthesized, or produced through DNA replication, reverse transcription, or a combination thereof. A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide sequence. The length of the oligonucleotide depends on how the oligonucleotide will be used. One skilled in the art would understand the approximate length of oligonucleotide necessary in any given method. Depending on the method, an oligonucleotide may be 1 to 1000 bases in length. In other aspects, it may be 5 to 500 bases in length, 5 to 100 bases in length, 5 to 50 bases in length, or 10 to 30 bases in length.

When a particular species or strain specific sequence is identified, strain specific probes or primer sets may be designed based on any part of that sequence. The probes or primers may be the entirety of that sequence. The probes or primers may also comprise part of or the entirety of that sequence along with other sequences or one or more additional nucleotides. The primers or probes designed according to particular species or strain sequence may also be represented in degenerate form, or comprising chemically modified nucleic acids, or any other components that facilitate the identification of the identifying sequence of a strain or species. The concept of a sequence identified to be specific to a species or strain further encompasses nucleic acid sequences that are less than 100% identical to the specific sequence, but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence may still be encompassed by the invention if it is capable of binding to its complimentary sequence and/or facilitating nucleic acid amplification of a desired target sequence.

The term "primer" refers to an oligonucleotide, whether occurring naturally as in a purified restriction digest or produced synthetically, which is capable of acting as a point of initiation of nucleic acid synthesis when placed under conditions in which synthesis of a primer extension product complementary to a template nucleic acid strand is induced, i.e., in the presence of nucleotides and an inducing agent such as DNA polymerase and at a suitable temperature and pH. The primer is preferably single-stranded for maximum efficiency in amplification. Alternatively, the primer is first treated to ensure that it is single-stranded before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The strain specific sequences identified in various MRSA strains, including USA 100, 300, and 600, are disclosed in Table A, as SEQ ID NOs. 1, 3, 5 and 7. Specifically, each of these strain specific sequences comprises a strain specific single nucleotide polymorphism (SNP), also called allelic identification herein, signifying the identity of a known or unknown MRSA strain. Loci in the FPR3757 reference genome with nucleotide variations containing allelic identifications include: 1531501=A or C; 1069320=A or G; 1053462=T or A; and 2595222=G or A, each of which represents the corresponding strain name listed in the first column in Table A. The concept of "allele" or "allelic" is detailed below.

identifies the host as a non-USA300 MRSA strain; 1069320=A allele identifies the host as a PFGE USA300 MRSA strain, whereas 1069320=G identifies the host as a non-USA300 MRSA strain; 1053462=T allele identifies the host as a PFGE USA600 MRSA strain, whereas 1053462=A identifies the host as a non-USA600 MRSA strain; and 2595222=G allele identifies the host as a PFGE USA100 MRSA strain, whereas 2595222=A identifies the host as a non-USA10 MRSA strain (see Table A).

(iii) Biomarkers as Indications of the Presence of Specific Species or Strain

Molecules, including but not limited to small RNAs, peptides and proteins, derived from transcription or translation

TABLE A

Allelic identification using SNPs for various MRSA strains.

| Strain name | Sequence name | Sequence containing strain specific SNP | SNP location in FPR3757 reference genome | SEQ ID NO. |
|---|---|---|---|---|
| USA300_153 | 153_USA300-A | ATAATAACATACGCTTCA | 1531501 | 1 |
| Non-USA300_153 | 153_non300-C | ATAATAACATCCGCTTCA | | 2 |
| USA300_106 | 106_USA300-A | CAATTATCCAACCGAGTG | 1069320 | 3 |
| Non-USA300_106 | 106_non300-G | CAATTATCCAACCGGGTG | | 4 |
| USA600_105 | 105_USA600-T | TAGTCATTTTTCCTGCATAA | 1053462 | 5 |
| Non-USA600_105 | 105_non600-A | TAGTCATTTTACCTGCATAA | | 6 |
| USA100_259 | 259_USA100-G | TGTAACTTTCTGGGCCT | 2595222 | 7 |
| Non-USA100_259 | 259_non100-A | TGTAACTTTCTGGACCT | | 8 |

(ii) Alleles of Species or Strain Specific Nucleic Acids

Identifying alleles specific to a MRSA strain is another aspect of this invention. An allele includes any form of a particular nucleic acid that may be recognized as a form of existence of a particular nucleic acid on account of its location, sequence, modification, or any other characteristics that may identify it as being a particular existing form of that particular nucleic acid.

Alleles include but need not be limited to forms of a nucleic acid that include point mutations, deletions, single nucleotide polymorphisms (SNPs), inversions, translocations, heterochromatic insertions, and differentially methylated sequences relative to a reference gene, whether alone or in combination. When a particular nucleic acid is a gene, the allele of this particular gene may or may not produce a functional protein; the functional protein thereof may or may not comprise a silent mutation, frame-shift mutation. The different alleles of a particular gene may each produce a protein with altered function, localization, stability, dimerization, or protein-protein interaction; may have overexpression, underexpression or no expression; may have altered temporal or spacial expression specificity. The presence or absence of an allele may be detected through the use of any process known in the art, including using primers and probes designed accordingly for PCR, sequencing, hybridization analyses. An allele may also be called a mutation or a mutant. An allele may be compared to another allele that may be termed a wild type form of an allele. In some cases, the wild type allele is more common than the mutant.

As disclosed herein, 1531501=A allele identifies the host as a PFGE USA300 MRSA strain, whereas 1531501=C allele processes of various MRSA strains specific to nucleic acid sequence alleles may serve as biomarkers indicating the presence of a particular species or strain. Some molecules that are produced by the immune system to defend against a particular MRSA strain, for example, may also serve as biomarkers. The presence of a particular species or strain may be indicated by the presence or absence of the biomarker, or a differential level of the biomarker. In one embodiment, the presence or absence of the biomarker may be determined by PCR, hybridization, sequencing, or any other methods known in the art. In one embodiment, methods of detecting an allele generally involve assessing the expression of material created from a genomic DNA template such as an RNA or protein molecule. Such expression may be assessed by any of a number of methods used currently in the art and yet to be developed.

Once strain specific genes, alleles thereof, or other nucleic acid based biomarkers thereof, are identified, primers and probes may be designed to screen samples to specifically and selectively detect the presence or absence of these genes, alleles or biomarkers, and therefore, a particular strain of *Staphylococcus* may be determined through various methods including PCR-based (polymerase chain reaction-based) methods such as real-time PCR, quantitative PCR, quantitative real time PCR; allele specific ligation; comparative genomic hybridization; sequencing; and other methods known in the art. One aspect of the invention provides primers based on strain specific sequences in Table A for real-time PCR assays comprising one or more specific primer sets and probes depending on the application to differentiate between various MRSA strains.

As to probes, they may be used for single probe analysis or multiplex probe/primer combined Real Time-PCR/PCR analysis. Oligonucleotide probes complimentary to a selected sequence within the target sequence may be designed. In one exemplary example, oligonucleotide probes facilitating Real Time-PCR/PCR product detection are complimentary to a selected sequence within the target sequence downstream from either the upstream or downstream primer. Therefore, these probes hybridize to an internal sequence of the amplified fragment of a targeted sequence.

One aspect of the present invention provides assays comprising primers and/or probes based on strain specific alleles that can be used to detect and/or differentiate different strains of MRSA, specifically USA100, USA300 and USA600 strains. An exemplary group of primers and probes based on strain specific alleles for detecting USA100 and non-USA100; USA300 and non-USA300; USA600 and non-USA600 is disclosed in Table B.

by SEQ ID NO. 15 is attached with 6FAM and MGBNFQ labels (e.g. 6FAM-CAATTATCCAACCGAGTGG-MGB-NFQ). In one embodiment, the probe represented by SEQ ID NO. 16 is attached with VIC and MGBNFQ labels (e.g. VIC-CAATTATCCAACCGGGTG-MGBNFQ).

In yet another embodiment, by applying primers represented by SEQ ID NO. 17 and 18 and/or probes represented by SEQ ID NO. 19 and 20, a USA600_105 assay may be carried out to identify and differentiate MRSA USA600 and non-USA600 strains. In one embodiment, the probe represented by SEQ ID NO. 19 is attached with 6FAM and MGB-NFQ labels (e.g. 6FAM-TAGTCATTTTTCCTGCATAA-MGBNFQ). In one embodiment, the probe represented by SEQ ID NO. 20 is attached with VIC and MGBNFQ labels (e.g. VIC-TAGTCATTTTACCTGCATAA-MGBNFQ).

TABLE B

Allelic discrimination assays and primer/probe sets

| Assay | Primer/probe name (with exemplary label) | Primer/probe sequence | Assay amplicon size(bp) | SEQ ID NO. |
|---|---|---|---|---|
| USA300_153 | 153_USA300_F | TCAATCCTTCACGCACGTTAAC | 72 | 9 |
|  | 153_USA300_R | GAGCGCAGGCAGAAATCG |  | 10 |
|  | 153_USA300-A_FAM | ATAATAACATACGCTTCATC |  | 11 |
|  | 153_non300-C_VIC | AAATAATAACATCCGCTTCA |  | 12 |
| USA300_106 | 106_USA300_F | AGTTGAACTTGCAGCACAACATG | 117 | 13 |
|  | 106_USA300_R | CCTGTGACTACCATTGCAATACCA |  | 14 |
|  | 106_USA300-A_FAM | CAATTATCCAACCGAGTGG |  | 15 |
|  | 106_non300-C_VIC | CAATTATCCAACCGGGTG |  | 16 |
| USA600_105 | 105_USA600_F | AAACAAGAGGCAATTCAAATAACTCA | 91 | 17 |
|  | 105_USA600_R | GGTACCCTATTTGCGACACTATTAACT |  | 18 |
|  | 105_USA600-T_FAM | TAGTCATTTTTCCTGCATAA |  | 19 |
|  | 105_non600-A_VIC | TAGTCATTTTACCTGCATAA |  | 20 |
| USA100_259 | 259_USA100_F | TCGTAATAACGATCACTGGCAAT | 140 | 21 |
|  | 259_USA100_R | GGCTTTCTTTCTAACTGCATTACCA |  | 22 |
|  | 259_USA100-G_FAM | TGTAACTTTCTGGGCCT |  | 23 |
|  | 259_non100-A_VIC | TGTAACTTTCTGGACCTGT |  | 24 |

As shown in Table B, the present invention provides, in one embodiment, that by applying primers represented by SEQ ID NO. 9 and 10 and/or probes represented by SEQ ID NO. 11 and 12, a USA300_153 assay may be carried out to identify and differentiate MRSA USA300 and non-USA300 strains. In one embodiment, the probe represented by SEQ ID NO. 11 is attached with 6FAM and MGBNFQ labels (e.g. 6FAM-ATAATAACATACGCTTCATC-MGBNFQ). In one embodiment, the probe represented by SEQ ID NO. 12 is attached with VIC and MGBNFQ labels (e.g. VIC-AAATAATAA-CATCCGCTTCA-MGBNFQ).

In another embodiment, by applying primers represented by SEQ ID NO. 13 and 14 and/or probes represented by SEQ ID NO. 15 and 16, a USA300_106 assay may be carried out to identify and differentiate MRSA USA300 and non-USA300 strains. In one embodiment, the probe represented In still another embodiment, by applying primers represented by SEQ ID NO. 21 and 22 and/or probes represented by SEQ ID NO. 23 and 24, a USA100_259 assay may be carried out to identify and differentiate MRSA USA100 and non-USA100 strains. In one embodiment, the probe represented by SEQ ID NO. 23 is attached with 6FAM and MGB-NFQ labels (e.g. 6FAM-TGTAACTTTCTGGGCCT-MGB-NFQ). In one embodiment, the probe represented by SEQ ID NO. 24 is attached with VIC and MGBNFQ labels (e.g. VIC-TGTAACTTTCTGGACCTGT-MGBNFQ).

In one preferred embodiment, a multiplex assay comprising the USA600_105 assay, the USA100_259 assay, and one or both of the USA300_153 and USA300_106 assays may be used to identify and differentiate MRSA strains selected from a group consisting of MRSA USA100, USA300, USA600, non-USA100, non-USA300 and non-USA600 strains by applying corresponding primers and probes in one PCR or Real Time-PCR reaction.

The combination of assays in a multiplex Real Time-PCR/PCR assay is achieved through applying multiple sets of primers and/or probes, respectively, in one Real Time-PCR reaction. The multiplex Real Time-PCR/PCR assay may comprise any number or any combination of individual assays, even if some of the assays are redundant in purposes but serve as a verification tool.

In some other embodiments, the individual assays, such as USA300_153, USA300_106, USA600_105 and USA100_259, as disclosed herein, may also be carried out separately, i.e. in independent Real Time-PCR/PCR assays, such that each independent Real Time-PCR/PCR assay only has one pair of primers and corresponding probes specific for one MRSA strain. However the results of these individual assays may be superimposed and comparable after internal control normalization.

The primers or probes designed according to a particular strain specific sequence, or homologs thereof, may also be represented in degenerate form, or comprising chemically modified nucleic acids, or any other components that facilitate the identification of the identifying sequence of a strain or species. An oligonucleotide may be in any physical formulation including as a solid (including crystal salts as necessary,) or it may be in a solution such as in a buffered solution. The labels that can be attached to the primers or probes are detailed in Section II.

(b) Samples that May Contain Various MRSA Strains

Samples often come with a mixture of bacterium species. The present invention discloses assays utilizing primer sets and/or probes, methods and kits designed to differentiate among various MRSA strains, including the USA100, USA300 and USA600 strains, in a sample using a single assay comprising a single set of primers and/or corresponding probes, or a multiplex assay comprising a combination of variable sets of primers and/or corresponding probes depending on the application.

A sample subjected to the assays, methods or kits disclosed herein may or may not be suspected of containing a nucleic acid from a bacterium of interest. Nucleic acids may include but need not be limited to RNA, cDNA, tRNA, mitochondrial DNA, plasmid DNA, siRNA, genomic DNA, or any other naturally occurring or artificial nucleic acid molecule originating from a bacterium. Samples may be suspected of containing a bacterium if they are derived from a subject displaying symptoms of a bacterial infection, or from an environmental sample from an area in which a bacterium is thought to be endemic, or from a subject recently present in a hospital or other environment found to contain MRSA. A subject may or may not display signs or symptoms of MRSA infection, which include red, swollen and painful areas on the skin, drainage of pus or other fluids from the site, fever, skin abscesses, warmth around the infected area, chest pain, chills, cough, fatigue, malaise, headache, muscle ache, rash, and shortness of breath.

A sample may be derived from anywhere that a bacterium or any part of a bacterium may be found, including but not limited to soil, air, water, solid surfaces (whether natural or artificial,) culture media, foodstuffs, devices, including devices used in medical procedures and/or bodily embellishment procedures (such as tattoo needles or body piercing needles). Additionally, a sample may be derived from a subject, or from agricultural, environmental, or any and all other sources.

A subject may be any organism that may be infected by a bacterium, such as plants and animals, including but not limited to humans, companion animals, such as dogs, cats, birds, or small mammals, livestock animals such as cattle, pigs, sheep, poultry, and any other domesticated or wild animal. Samples derived from subjects include, but are not limited to, a nucleic acids in all forms, biopsy or other in vivo or ex vivo analysis of, e.g., prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample, such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a bacterium, or any part of a bacterium might be present.

Samples may be collected by any and all methods now known or yet to be disclosed, including, e.g., swiping or swabbing an area or orifice, removal of a piece of tissue as in a biopsy, any method known to collect bodily fluids, wiping down a surface, collecting a sample of liquid, collecting an air sample, or any other method that may be used to collect bacteria in such a way as to preserve biological material such as DNA, RNA or protein for analysis.

(II) Methods for Detecting MRSA Strains

Methods that can be used to identify strain specific nucleic acids, alleles of strain specific nucleic acids, and biomarkers derived from transcriptional and translational products of the strain specific nucleic acids and the alleles thereof, include PCR, Real Time-PCR, hybridization, sequencing and any combination of the above methods. In one embodiment, the presence of the PCR or Real Time-PCR products in an assay may indicate the presence of one or more MRSA strain(s). In one embodiment, the PCR or Real Time-PCR products may be further identified or differentiated by hybridization undergoing simultaneously or subsequently with the PCR reactions. In another embodiment, the PCR or Real Time-PCR products may be sequenced to ascertain the existence of a particular allele indicative of the identity of the one or more MRSA strains in a sample.

A nucleic acid may be added to a sample by any of a number of methods, including manual methods, mechanical methods, or any combination thereof. The presence of the allele may be signified by any of a number of methods, including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

(a) PCR

Nucleic acids may be selectively and specifically amplified from a template nucleic acid contained in a sample. In some nucleic amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with Klenow or any other RNA polymerase, or any other method by which copies of a desired sequence are generated.

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.) an annealing stage with a temperature that is selected based on the melting temperature (Tm) of the primers and the degeneracy of the primers, and an extension stage (for example 40-75' C). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complimentary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes, as described above, will allow a quantification of the amount of specific template DNA present in the initial sample. In addition, RNA may be detected by PCR analysis by first creating a DNA template from RNA through a reverse transcriptase enzyme. In some aspects of the invention, the allele may be detected by quantitative PCR analysis facilitating genotyping analysis of the samples.

As an exemplary example, the use of dual-labeled oligonucleotide probes in PCR reactions is disclosed in U.S. Pat. No. 5,716,784 to DiCesare. In the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

Template specificity is achieved in most amplification techniques by the choice of enzyme. Amplification enzymes are enzymes that, under the conditions in which they are used, will process only specific sequences of nucleic acid in a heterogeneous mixture of nucleic acid. Other nucleic acid will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template."

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

One aspect of the invention provides a multiplex PCR assay to identify and differentiate MRSA strains. Multiplex PCR is a technique for amplification of multiple targets in a single PCR experiment. In a multiplexing assay, more than one target sequence can be amplified by using multiple primer pairs in a reaction mixture. As an extension to the practical use of PCR, this technique has the potential to produce considerable savings in time and effort within the laboratory without compromising on the utility of the experiment. Design of specific primer sets is essential for a successful multiplex reaction, and the factors to be considered include primer length, melting temperature, specificity, and primer dimerization.

In some forms of multiplex PCR assays, relative quantification is often used to determine the changes in steady-state mRNA levels of a gene across multiple samples, and describe the level of mRNA in reference to the levels of an internal control RNA. The control RNA may be co-amplified in the same tube in a multiplex assay or may be amplified in a separate tube. Generally, the control RNA may be a house keeping gene, or gene with constitutive expression, or a standard with known concentration. In relative quantification, however, it does not require standards with known concentrations and the reference can be any transcript, as long as its sequence is known. Relative quantification is based on the expression levels of a target gene versus one or more reference gene(s), and in many experiments, it is adequate for investigating physiological changes in gene expression levels. To calculate the expression of a target gene in relation to an adequate reference gene, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in Real Time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. Cp value represents the cycle at which the increase of fluorescence is highest and where the logarithmic phase of a PCR begins. The LightCycler® 480 Software (Roche Applied Science, Penzberg, Germany) calculates the second derivatives of entire amplification curves and determines where this value is at its maximum. By using the second-derivative algorithm, data obtained are more reliable and reproducible, even if fluorescence is relatively low.

(b) Hybridization

In addition to PCR, genotyping analysis may also be performed using a probe that is capable of hybridizing to a nucleic acid sequence of interest. The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence that is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (in other words, it is the complement of) the single-stranded nucleic acid sequence under conditions of low to high stringency as described above.

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

Probes for hybridization may comprise nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide. The description of oligonucleotide, as described herein.

Under some circumstances, methods of detecting a gene or an allele may involve assessing their expression level through their transcriptional or translational products such as a RNA or protein molecule. The expression of a gene or an allele may be assessed by any of a number of methods used currently in the art and yet to be developed. Examples include any nucleic acid detection method, including the following nonlimiting examples, microarray analysis, RNA in situ hybridization, RNAse protection assay, Northern blot. Other examples include any process of detecting expression that uses an antibody including the following nonlimiting examples, flow cytometry, immunohistochemistry, ELISA, Western blot, Northwestern blot, and immunoaffinity chromatography. Antibodies may be monoclonal, polyclonal, or any antibody fragment, for example, Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

In some aspects of the invention, the presence of an allele may be established by binding to probes in a media or on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subjected to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye from differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof, or any other compound that may be differentially detected. The label may also include one or more fluorescent dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ. Exemplary labels incorporated in probes in each assay are presented in TABLE B and Section I.

(c) Sequencing

Methods of detecting the presence of a gene or an allele further include, but are not limited to, any form of DNA sequencing including Sanger, next generation sequencing, pyrosequencing, SOLID sequencing, massively parallel sequencing, pooled, and barcoded DNA sequencing or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides, or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfurylase enzyme converts pyrophosphate into ATP which, in turn, catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence, and alternatively, a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

(III) Kits.

Still another aspect of the invention encompasses kits for identifying and differentiating MRSA strains including USA100, USA300 and USA600. In preferred embodiments, the kits comprise one or more primer sets and probes for assays selected from a group consisting of USA300_153 assay, USA300_106 assay, USA600_105 assay, and USA100_259 assay. As described in detail in previous sections and in Table B: USA300_153 assay for identifying and differentiating MRSA USA300 and non-USA300 strains by applying primers represented by SEQ ID NO. 9 and 10, and/or probes, represented by SEQ ID NO. 11 and 12; USA300_106 assay for identifying and differentiating MRSA USA300 and non-USA300 strains by applying primers represented by SEQ ID NO. 13 and 14, and/or probes represented by SEQ ID NO. 15 and 16; USA600_105 assay for identifying and differentiating MRSA USA600 and non-USA600 strains by applying primers represented by SEQ ID NO. 17 and 18, and/or probes represented by SEQ ID NO. 19 and 20; USA100_259 assay for identifying and differentiating MRSA USA100 and non-USA100 strains by applying primers represented by SEQ ID NO. 21 and 22, and/or probes represented by SEQ ID NO. 23 and 24.

The multiplex assay is a type of analysis chosen from PCR, Real Time-PCR, sequencing, hybridization, and any combination thereof, in which primer sets and/or probes are applied to detect the presence or absence of strain specific signatures. The assays detecting respective targeted strain specific signatures may be carried out individually in separate reaction systems, or as a multiplex assay in one combined and mixed reaction system for PCR, Real Time-PCR, sequencing, hybridization, or any combination thereof.

In one preferred embodiment, the kit comprises primer sets and probes for a multiplex assay, which comprises corresponding primers and probes for USA600_105 assay, USA100_259 assay and one or both of USA300_153 and USA300_106 assays.

The kits that facilitate nucleic acid based assays may further comprise one or more of the following: nucleic acid extraction reagents, controls, disposable cartridges, labeling reagents, enzymes including PCR amplification reagents such as the DNA polymerases Taq or Pfu, reverse transcriptase, or one or more other polymerases, and/or reagents that facilitate hybridization.

In another embodiment, the kit may further comprise a label that can be used to label the primer or probe oligonucleotide. A label may be any substance capable of aiding a machine, detector, sensor, device, or enhanced or unenhanced human eye, in differentiating a sample that displays positive expression from a sample that displays reduced expression or no expression at all. Examples of labels include, but are not limited to: a radioactive isotope or chelate thereof, a dye (fluorescent or nonfluorescent,) stain, enzyme, or nonradioactive metal. Specific examples include, but are not limited to: fluorescein, biotin, digoxigenin, alkaline phosphatase, biotin, streptavidin, $^3H$, $^{14}C$, $^{32}P$, $^{35}S$, or any other compound capable of emitting radiation, rhodamine, 4-(4'-dimethylaminophenylazo)benzoic acid ("Dabcyl"); 4-(4'-dimethylaminophenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra-acetic acid ("EDTA") and derivatives thereof, or any other compound that signals the presence of the labeled nucleic acid. In one embodiment of the invention, the label includes one or more dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ.

In yet another embodiment, the primers and probes in the kit may have been labeled, and can be applied without a labeling process in PCR, sequencing reaction, or binding to a solid substrate such as oligonucleotide array. In one embodiment, the probe represented by SEQ ID NO. 11 is attached with 6FAM and MGBNFQ labels (e.g. 6FAM-ATAATAA-CATACGCTTCATC-MGBNFQ). In one embodiment, the probe represented by SEQ ID NO. 12 is attached with VIC and MGBNFQ labels (e.g. VIC-AAATAATAACATCCGCT-TCA-MGBNFQ). In one embodiment, the probe represented by SEQ ID NO. 15 is attached with 6FAM and MGBNFQ labels (e.g. 6FAM-CAATTATCCAACCGAGTGG-MGBNFQ). In one embodiment, the probe represented by SEQ ID NO. 16 is attached with VIC and MGBNFQ labels (e.g. VIC-CAATTATCCAACCGGGTG-MGBNFQ). In one embodiment, the probe represented by SEQ ID NO. 19 is attached with 6FAM and MGBNFQ labels (e.g. 6FAM-TAGTCATTTTTCCTGCATAA-MGBNFQ). In one embodiment, the probe represented by SEQ ID NO. 20 is attached with VIC and MGBNFQ labels (e.g. VIC-TAGT-CATTTTACCTGCATAA-MGBNFQ). In one embodiment, the probe represented by SEQ ID NO. 23 is attached with 6FAM and MGBNFQ labels (e.g. 6FAM-TG-TAACTTTCTGGGCCT-MGBNFQ). In one embodiment, the probe represented by SEQ ID NO. 24 is attached with VIC and MGBNFQ labels (e.g. VIC-TGTAACTTTCTGGAC-CTGT-MGBNFQ).

A kit for identifying and differentiating MRSA USA100, USA300 and USA600 strains in a sample may also comprise instructions for use. In one embodiment, the kit may further comprise an indication that links the output of the assays provided by the kit to a particular result. For example, an indication may provide guidance to associate the presence or absence of one or more sequences to the identification of a particular bacterial phylum, class, order, family, genus species, subspecies, strain, or any other delineation of a group of bacteria. The indication may contain a standard curve configured to quantify the amount of bacterium present in a sample. The output of the assay may be in the form of a particular sequence, a particular genotype, a particular Ct level in a real-time quantitative PCR reaction, a level of fluorescence or radioactive decay, a value derived from a standard curve, or from a positive or negative control, or any combination of these and other outputs. The indication may be printed on a writing that may be included in the kit, or it may be posted on the Internet, or embedded in a software package. The writing may include graphical depictions of results such as a photomicrograph or amplification plot.

A kit for identifying and differentiating MRSA USA100, USA300 and USA600 strains in a sample may further comprise a device used to collect the sample. Such devices may include but need not be limited to: swabs, needles, blood collection tubes, wipes, or any other apparatus that may be used to collect a biological sample from a patient or from the environment now known or yet to be disclosed.

EXAMPLES

The following examples illustrate certain aspects of the invention.

Example 1

Specificity and Selectivity

The present invention discloses PCR assays designed to differentiate between MRSA USA100, USA300 and USA600 strains using single assays or multiplex assays comprising two or more sets of strain specific primers and corresponding primers thereof depending on the application. The validation data of the four disclosed MRSA USA strain assays across DNA from various MRSA strains were shown in Table 1. Among the 92 samples, there were 5 discordant samples, that is, the allele call based on various assays disclosed herein does not match with the strain type of the isolate which was originally typed using PFGE. The PFGE strain types are indicated in the first column in Table 1. The performance of the individual single assays using panels of bacterial isolates is shown in Tables 2-5. All of the assays have been shown to be highly sensitive and specific.

TABLE 1

Validation data of 4 MRSA USA strain assays across DNA from various MRSA strains

| MRSA strain genomic DNA | USA600_105 Allele call | USA100_259 Allele call | USA300_106 Allele call | USA300_153 Allele call | Strain type and Allele call match? | Discordance (Strain type/ Allele call) |
|---|---|---|---|---|---|---|
| A01 NARSA-642_USA100 (TG09412) | non-600 | USA100 | non-300 | non-300 | Y | |
| A02 NARSA-650_USA100 (TG09319) | non-600 | non-100 | USA300 | USA300 | No | USA 100/ USA300 |

TABLE 1-continued

Validation data of 4 MRSA USA strain assays across DNA from various MRSA strains

| MRSA strain genomic DNA | USA600_105 Allele call | USA100_259 Allele call | USA300_106 Allele call | USA300_153 Allele call | Strain type and Allele call match? | Discordance (Strain type/ Allele call) |
|---|---|---|---|---|---|---|
| A04 NARSA-667_USA300 (TG09336) | non-600 | non-100 | USA300 | USA300 | Y | |
| A05 NARSA-674_USA100 (TG09343) | non-600 | USA100 | non-300 | non-300 | Y | |
| A06 NARSA-681_USA100 (TG09350) | non-600 | USA100 | non-300 | non-300 | Y | |
| A07 NARSA-688_USA300 (TG09357) | non-600 | non-100 | USA300 | USA300 | Y | |
| A08 NARSA-696_USA100 (TG09365) | non-600 | USA100 | non-300 | non-300 | Y | |
| A09 NARSA-705_USA100 (TG09374) | non-600 | USA100 | non-300 | NS | Y | |
| A10 NARSA-712_USA100 (TG09381) | non-600 | USA100 | non-300 | non-300 | Y | |
| A11 NARSA-719_USA100 (TG09388) | non-600 | USA100 | non-300 | non-300 | Y | |
| A12 NARSA-728_USA100 (TG09397) | non-600 | USA100 | non-300 | non-300 | Y | |
| B01 NARSA-643_USA300 (TG09413) | non-600 | non-100 | USA300 | USA300 | Y | |
| B02 NARSA-651_USA200 (TG09320) | non-600 | non-100 | non-300 | non-300 | Y | |
| B03 NARSA-659_USA300 (TG09328) | non-600 | USA100 | non-300 | non-300 | No | USA300/ USA100 |
| B05 NARSA-675_USA800 (TG09344) | non-600 | non-100 | non-300 | non-300 | Y | |
| B06 NARSA-682_USA100 (TG09351) | non-600 | USA100 | non-300 | non-300 | Y | |
| B07 NARSA-689_USA700 (TG09358) | non-600 | non-100 | non-300 | non-300 | Y | |
| B08 NARSA-697_USA100 (TG09366) | non-600 | USA100 | non-300 | non-300 | Y | |
| B09 NARSA-706_USA100 (TG09375) | non-600 | USA100 | non-300 | NS | Y | |
| B10 NARSA-713_USA100 (TG09382) | non-600 | USA100 | non-300 | non-300 | Y | |
| B11 NARSA-720_USA100 (TG09389) | non-600 | USA100 | non-300 | non-300 | Y | |
| B12 NARSA-729_USA300 (TG09398) | non-600 | non-100 | USA300 | USA300 | Y | |
| C01 NARSA-644_USA100 (TG09414) | non-600 | USA100 | non-300 | non-300 | Y | |
| C02 NARSA-652_USA1000 (TG09321) | non-600 | non-100 | non-300 | non-300 | Y | |
| C03 NARSA-660_USA100 (TG09329) | non-600 | non-100 | USA300 | USA300 | No | USA 100/ USA300 |
| C04 NARSA-668_USA800 (TG09337) | non-600 | non-100 | USA300 | USA300 | Y | |
| C06 NARSA-683_USA300 (TG09352) | non-600 | non-100 | USA300 | USA300 | Y | |
| C07 NARSA-690_USA100 (TG09359) | non-600 | USA100 | non-300 | non-300 | Y | |
| C08 NARSA-700_USA100 (TG09369) | non-600 | USA100 | non-300 | non-300 | Y | |
| C09 NARSA-707_USA300 (TG09376) | non-600 | non-100 | USA300 | NS | Y | |
| C10 NARSA-714_USA800 (TG09383) | non-600 | non-100 | non-300 | non-300 | Y | |
| C11 NARSA-721_USA100 (TG09390) | non-600 | USA100 | non-300 | non-300 | Y | |
| C12 NARSA-730_USA1000 (TG09399) | non-600 | non-100 | non-300 | non-300 | Y | |
| D01 NARSA-645_Iberian (TG09314) | non-600 | non-100 | non-300 | non-300 | Y | |
| D02 NARSA-653_USA800 (TG09322) | non-600 | USA100 | non-300 | non-300 | No | USA800/ USA100 |
| D03 NARSA-661_USA100 (TG09330) | non-600 | USA100 | non-300 | non-300 | Y | |

TABLE 1-continued

Validation data of 4 MRSA USA strain assays across DNA from various MRSA strains

| MRSA strain genomic DNA | USA600_105 Allele call | USA100_259 Allele call | USA300_106 Allele call | USA300_153 Allele call | Strain type and Allele call match? | Discordance (Strain type/ Allele call) |
|---|---|---|---|---|---|---|
| D04 NARSA-669_USA100 (TG09338) | non-600 | USA100 | non-300 | non-300 | Y | |
| D05 NARSA-676_USA1000 (TG09345) | non-600 | non-100 | non-300 | non-300 | Y | |
| D07 NARSA-691_USA500 (TG09360) | non-600 | non-100 | non-300 | non-300 | Y | |
| D08 NARSA-701_USA200 (TG09370) | non-600 | non-100 | non-300 | non-300 | Y | |
| D09 NARSA-708_USA500 (TG09377) | non-600 | non-100 | non-300 | NS | Y | |
| D10 NARSA-715_USA600 (TG09384) | USA600 | non-100 | non-300 | non-300 | Y | |
| D11 NARSA-722_USA200 (TG09391) | non-600 | non-100 | non-300 | non-300 | Y | |
| D12 NARSA-731_USA300 (TG09400) | non-600 | non-100 | USA300 | USA300 | Y | |
| E01 NARSA-646_USA100 (TG09315) | non-600 | USA100 | non-300 | non-300 | Y | |
| E02 NARSA-655_USA300 (TG09324) | non-600 | non-100 | USA300 | USA300 | Y | |
| E03 NARSA-662_USA300 (TG09331) | non-600 | non-100 | USA300 | USA300 | Y | |
| E04 NARSA-670_USA100 (TG09339) | non-600 | USA100 | non-300 | non-300 | Y | |
| E05 NARSA-677_USA300 (TG09346) | non-600 | non-100 | USA300 | USA300 | Y | |
| E06 NARSA-684_USA300 (TG09353) | non-600 | non-100 | USA300 | USA300 | Y | |
| E08 NARSA-702_USA300 (TG09371) | non-600 | non-100 | USA300 | USA300 | Y | |
| E09 NARSA-709_USA100 (TG09378) | non-600 | USA100 | non-300 | NS | Y | |
| E10 NARSA-716_USA300 (TG09385) | non-600 | non-100 | USA300 | USA300 | Y | |
| E11 NARSA-723_USA100 (TG09392) | non-600 | USA100 | non-300 | non-300 | Y | |
| E12 NARSA-732_USA300 (TG09401) | non-600 | non-100 | USA300 | USA300 | Y | |
| F01 NARSA-647_USA300 (TG9316) | non-600 | non-100 | USA300 | USA300 | Y | |
| F02 NARSA-656_USA100 (TG09325) | non-600 | USA100 | non-300 | non-300 | Y | |
| F03 NARSA-663_USA100 (TG09332) | non-600 | USA100 | non-300 | non-300 | Y | |
| F04 NARSA-671_USA100 (TG09340) | non-600 | USA100 | non-300 | non-300 | Y | |
| F05 NARSA-678_USA500 (TG09347) | non-600 | non-100 | non-300 | non-300 | Y | |
| F06 NARSA-685_USA500 (TG09354) | non-600 | non-100 | non-300 | non-300 | Y | |
| F07 NARSA-692_USA800 (TG09361) | non-600 | non-100 | non-300 | non-300 | Y | |
| F09 NARSA-710_USA100 (TG09379) | non-600 | USA100 | non-300 | NS | Y | |
| F10 NARSA-717_USA100 (TG09386) | non-600 | USA100 | non-300 | non-300 | Y | |
| F11 NARSA-724_USA300 (TG09393) | non-600 | non-100 | USA300 | USA300 | Y | |
| F12 NARSA-733_USA300 (TG09402) | non-600 | non-100 | USA300 | USA300 | Y | |
| G01 NARSA-648_USA600 (TG09317) | non-600 | USA100 | non-300 | non-300 | No | USA600/ USA100 |

TABLE 1-continued

Validation data of 4 MRSA USA strain assays across DNA from various MRSA strains

| MRSA strain genomic DNA | USA600_105 Allele call | USA100_259 Allele call | USA300_106 Allele call | USA300_153 Allele call | Strain type and Allele call match? | Discordance (Strain type/ Allele call) |
|---|---|---|---|---|---|---|
| G02 NARSA-657_USA300 (TG09326) | non-600 | non-100 | USA300 | USA300 | Y | |
| G03 NARSA-665_USA100 (TG9334) | non-600 | USA100 | non-300 | non-300 | Y | |
| G04 NARSA-672_USA100 (TG09341) | non-600 | USA100 | non-300 | non-300 | Y | |
| G05 NARSA-679_USA100 (TG09348) | non-600 | USA100 | non-300 | non-300 | Y | |
| G06 NARSA-686_Iberian (TG09355) | non-600 | non-100 | non-300 | non-300 | Y | |
| G07 NARSA-693_USA300 (TG09362) | non-600 | non-100 | USA300 | USA300 | Y | |
| G08 NARSA-703_USA300 (TG09372) | non-600 | non-100 | USA300 | USA300 | Y | |
| G10 NARSA-718_USA100 (TG09387) | non-600 | USA100 | non-300 | non-300 | Y | |
| G11 NARSA-725_USA300 (TG09394) | non-600 | non-100 | USA300 | USA300 | Y | |
| G12 NARSA-735_USA100 (TG09404) | non-600 | USA100 | non-300 | non-300 | Y | |
| H01 NARSA-649_USA100 (TG09318) | non-600 | USA100 | non-300 | non-300 | Y | |
| H02 NARSA-658_USA100 (TG09327) | non-600 | USA100 | non-300 | non-300 | Y | |
| H03 NARSA-666_USA100 (TG09335) | non-600 | USA100 | non-300 | non-300 | Y | |
| H04 NARSA-673_USA100 (TG09342) | non-600 | USA100 | non-300 | non-300 | Y | |
| H05 NARSA-980_USA100 (TG09349) | non-600 | USA100 | non-300 | non-300 | Y | |
| H06 NARSA-687_USA300 (TG09356) | non-600 | non-100 | USA300 | USA300 | Y | |
| H07 NARSA-695_USA100 (TG09364) | non-600 | USA100 | non-300 | non-300 | Y | |
| H08 NARSA-704_USA100 (TG09373) | non-600 | USA100 | non-300 | non-300 | Y | |
| H09 NARSA-711_USA100 (TG09380) | non-600 | USA100 | non-300 | NS | Y | |
| H11 NARSA-727_USA100 (TG09396) | non-600 | USA100 | non-300 | non-300 | Y | |
| H12 NARSA-736_USA300 (TG09405) | non-600 | non-100 | USA300 | USA300 | Y | |
| BAA-1685_USA600 (TG10430) | USA600 | NS | NS | NS | Y | |
| BAA-1751_USA600 (TG10409) | USA600 | NS | NS | NS | Y | |
| BAA-1754_USA600 (TG10445) | USA600 | NS | NS | NS | Y | |
| USA 600-99758 uk MRs (TG00358) | USA600 | NS | NS | NS | Y | |

NS, Not screened

TABLE 2

USA100_259

| USA SNP Assay call | PFGE type | | USA assay characteristics | |
|---|---|---|---|---|
| | USA100 | Non-USA100 | | |
| USA100 | 42 | 3 | Sensitivity | 95.5% |
| Non-USA100 | 2 | 85 | Specificity | 96.6% |
| | | | Positive predicative value | 93.3% |
| | | | Negative predicative value | 97.7% |

TABLE 3

USA600_105

| USA SNP Assay call | PFGE type | | USA assay characteristics | |
|---|---|---|---|---|
| | USA600 | Non-USA600 | | |
| USA600 | 21 | 0 | Sensitivity | 95.5% |
| Non-USA600 | 1 | 92 | Specificity | 100.0% |
| | | | Positive predicative value | 100.0% |
| | | | Negative predicative value | 98.9% |

TABLE 4

| USA SNP | USA300_106 | | USA assay characteristics | |
|---|---|---|---|---|
| Assay call | USA300 | Non-USA300 | | |
| USA300 | 30 | 2 | Sensitivity | 93.8% |
| Non-USA300 | 2 | 86 | Specificity | 97.7% |
| | | | Positive predicative value | 93.8% |
| | | | Negative predictive value | 97.7% |

TABLE 5

| | USA300_153 | | | |
|---|---|---|---|---|
| | PFGE type | | USA assay characteristics | |
| | USA300 | Non-USA300 | | |
| USA300 | 30 | 2 | Sensitivity | 93.8% |
| Non-USA300 | 2 | 79 | Specificity | 97.5% |
| | | | Positive predicative value | 93.8% |
| | | | Negative predictive value | 97.5% |

Example 2

Multiplex Real-Time PCR Screening Using Cp Values

This example describes the procedure, equipment, and reagents required to perform a multiplex real-time PCR on the Lightcycler® 480 (Roche Applied Science, Penzberg, Germany) instrument to identify and differentiate MRSA USA100, USA300, and USA600 strains.

Items Required:

PerfeCTa® MultiPlex qPCR SuperMix (Quanta Cat#95063, Quanta Biosciences, Gaithersburg, Md.); Assay primers and probes; Molecular biology grade water; Microcentrifuge tubes; Optical reaction plates compatible with real-time instrument; Optical adhesive film and applicator; Micropipettes and tips; Template DNA and appropriate controls (gDNA from MRSA and CNS); Centrifuge with rotors for tubes and plates; Lightcycler® 480.

Reaction Preparation:

i. Color Compensation:

If running the assay for the first time on the instrument, a color compensation file must be generated. Reactions with at least 5 replicates of positive control DNA for each assay in singleton, and 5 total replicates of no template controls must be run. A color compensation file for this multiplex assay need only be generated once. See LC480 User's Manual for details. Prepare color compensation reactions as below.

ii. Assay Procedure:

(1) calculate volume of mastermix needed (Reaction volume×number samples×1.1); (2) mix reagents to that volume for a final reaction concentration of: 1× PerfeCTa® MultiPlex qPCR SuperMix; 300 nM forward primer; 300 nM reverse primer; 125 nM probe; add water to bring volume so final concentrations are reached upon addition of template; (3) transfer array mastermix into optical reaction plate; (4) add control template: add MRSA DNA template to each of the single assay reaction well; add water to no template control reaction wells. For subsequent runs on the same instrument, no single assays need to be run. The color compensation file generated previously can be applied to all subsequent multiplex assays using these fluorophores.

iii. Multiplex Setup:

(1) calculate volume of mastermix needed (reaction volume×number samples×1.1); (2) mix reagents to that volume for a final concentration of: 1× PerfeCTa® MultiPlex qPCR SuperMix; 300 nM each primer; 125 nM each probe; then add water to bring volume so final concentrations are reached upon addition of template; (3) transfer array mastermix into optical reaction plate; (4) add 0.5 to 10 ng DNA extracted from culture, and add more if DNA is extracted from specimens (optimization of template amount may be necessary); seal optical plate with optical adhesive film and spin down the liquid.

Thermal Cycling:

first, load plate onto instrument; then in LC480 software, create a new experiment with the following program: (1) in Detection Format menu select Multi Color Hydrolysis Probe; (2) select Customize and select colors accordingly; (3) enter proper reaction volume; (4) start run and name file. An exemplary program is illustrated here in Table 6:

TABLE 6

| Thermal cycling | | |
|---|---|---|
| Programs | | |
| Program Name | Cycles | Analysis mode |
| Hot start | 1 | None |
| Amplification | 40 | Quantification |
| Cooling | 1 | None |

| Temperature Targets | | | | |
|---|---|---|---|---|
| Target (° C.) | Acquisition Mode | Hold (hh:mm:ss) | Ramp Rate (° C./s) | Acquisitions (per ° C.) |
| Hot start | | | | |
| 95 | None | 0:03:00 | 4.8 | |
| Amplification | | | | |
| 95 | None | 0:00:15 | 4.8 | |
| 65 | Single | 0:01:00 | 2.5 | |
| Cooling | | | | |
| 40 | None | 0:00:10 | 2.5 | |

Software Setup for Color Compensation:

For the color compensation file generation, designate the color compensation reactions as follows: (1) in Sample Editor, then in Workflow menu, select Color Comp; (2) highlight positive control color comp samples from one assay; (3) choose the detector for that assay in the Dominant Channel pull-down menu; (4) click Make Replicates; (5) repeat for the other two assays; (6) highlight no template controls, and choose Water in the Dominant Channel menu; (7) create a subset which includes all color compensation reaction wells. After the above steps, the setup proceeds with normal software setup for naming samples and designating subsets for samples being run on the multiplex assay.

Analysis:

i. Color Compensation:

from the Create New Analysis menu, choose Color Compensation, and select the subset of color compensation reactions, then select Calculate; then Save this file to be applied to later analyses of this multiplex assay.

ii. Multiplex:

(1) from the Create New Analysis menu, choose Abx-Quant/$2^{nd}$ Derivative Max, and select the subset of samples to be analyzed; (2) in the Color Compensation pull-down menu choose In Database, then choose the color compensation file previously generated; (3) select Calculate and select reactions for which data are needed, then export results; (4) select the next color in Filter Comb and Calculate, then select reactions and export results; (5) repeat for last color.

---

What is claimed is:

1. A method of identifying and differentiating MRSA strains in a sample, comprising:
   receiving the sample;
   adding one or more strain specific primer sets, wherein each primer set comprises a first and a second isolated oligonucleotide, each comprising a sequence selected from the group consisting of SEQ ID NO. 9, SEQ ID NO. 10, SEQ ID NO. 13, SEQ ID NO. 14, SEQ ID NO. 17, SEQ ID NO. 18, SEQ ID NO. 21, and SEQ ID NO. 22 to a reaction mixture comprising the sample, wherein the first isolated oligonucleotide is different from the second isolated oligonucleotide;
   subjecting the mixture to conditions that allow nucleic acid amplification to produce amplification products; and
   identifying and differentiating MRSA isolates by obtaining an allelic identification of amplification products that signifies the sample as containing MRSA USA100, USA300, USA600, non-MRSA USA100, USA300, or USA600 strains.

2. The method of claim 1, wherein one of the strain specific primer sets comprises two oligonucleotides comprising SEQ ID NO. 9 and SEQ ID NO. 10, respectively.

3. The method of claim 1, wherein one of the strain specific primer sets comprises two oligonucleotides comprising SEQ ID NO. 13 and SEQ ID NO. 14, respectively.

4. The method of claim 1, wherein one of the strain specific primer sets comprises two oligonucleotides comprising SEQ ID NO. 17 and SEQ ID NO. 18, respectively.

5. The method of claim 1, wherein one of the strain specific primer sets comprises two oligonucleotides comprising SEQ ID NO. 21 and SEQ ID NO. 22, respectively.

6. The method of claim 1, wherein the step of adding one or more strain specific primer sets further comprises the step of adding a third and a fourth isolated oligonucleotide as probes corresponding to each strain specific primer set added, and the third or fourth oligonucleotide comprises a sequence selected from the group consisting of SEQ ID NO. 11, SEQ ID NO. 12, SEQ ID NO. 15, SEQ ID NO. 16, SEQ ID NO. 19, SEQ ID NO. 20, SEQ ID NO. 23, and SEQ ID NO. 24 to the reaction mixture comprising the sample;

wherein the third isolated oligonucleotide is different from the fourth isolated oligonucleotide; and wherein the third oligonucleotide comprises a first label, and the fourth oligonucleotide comprises a second label that is different from the first label.

7. The method of claim 6, wherein the third oligonucleotide comprises SEQ ID NO. 11 and the fourth oligonucleotide comprises SEQ ID NO. 12; and wherein the third and fourth oligonucleotides correspond to the strain specific primer set comprising two oligonucleotides comprising SEQ ID NO. 9 and SEQ ID NO. 10, respectively.

8. The method of claim 6, wherein the third oligonucleotide comprises SEQ ID NO. 15 and the fourth oligonucleotide comprises SEQ ID NO. 16; and wherein the third and fourth oligonucleotides correspond to the strain specific primer set comprising two oligonucleotides comprising SEQ ID NO. 13 and SEQ ID NO. 14, respectively.

9. The method of claim 6, wherein the third oligonucleotide comprises SEQ ID NO. 19 and the fourth oligonucleotide comprises SEQ ID NO. 20; and wherein the third and fourth oligonucleotides correspond to the strain specific primer set comprising two oligonucleotides comprising SEQ ID NO. 17 and SEQ ID NO. 18, respectively.

10. The method of claim 6, wherein the third oligonucleotide comprises SEQ ID NO. 23 and the fourth oligonucleotide comprises SEQ ID NO. 24; and wherein the third and fourth oligonucleotides correspond to the strain specific primer set comprising two oligonucleotides comprising SEQ ID NO. 21 and SEQ ID NO. 22, respectively.

11. The method of claim 6, wherein obtaining an allelic identification of amplification products further comprises the step of collecting signals from the first and the second labels.

12. The method of claim 1, wherein obtaining an allelic identification of amplification products further comprises the step of sequencing the amplification products.

13. The method of claim 12, wherein the sample containing a MRSA USA300 strain is signified by amplification products having an allelic identification comprising SEQ ID NO. 1 or SEQ ID NO. 3; or wherein the sample containing a MRSA non-USA300 strain is signified by amplification products having an allelic identification comprising SEQ ID NO. 2 or SEQ ID NO. 4.

14. The method of claim 12, wherein the sample containing a MRSA USA600 strain is signified by amplification products having an allelic identification comprising SEQ ID NO. 5; or wherein the sample containing a MRSA non-USA600 strain is signified by amplification products having an allelic identification comprising SEQ ID NO. 6.

15. The method of claim 12, wherein the sample containing a MRSA USA100 strain is signified by amplification products having an allelic identification comprising SEQ ID NO. 7; or wherein the sample containing a MRSA non-USA100 strain is signified by amplification products having an allelic identification comprising SEQ ID NO. 8.

\* \* \* \* \*

SEQUENCE LISTING

<160> NUMBER OF SEQ ID NOS: 24

<210> SEQ ID NO 1
<211> LENGTH: 18
<212> TYPE: DNA
<213> ORGANISM: Staphylococcus aureus

<400> SEQUENCE: 1
ataataacat acgcttca                                                 18

<210> SEQ ID NO 2
<211> LENGTH: 18
<212> TYPE: DNA
<213> ORGANISM: Staphylococcus aureus

<400> SEQUENCE: 2
ataataacat ccgcttca                                                 18

<210> SEQ ID NO 3
<211> LENGTH: 18
<212> TYPE: DNA
<213> ORGANISM: Staphylococcus aureus

<400> SEQUENCE: 3
caattatcca accgagtg                                                 18

<210> SEQ ID NO 4
<211> LENGTH: 18
<212> TYPE: DNA
<213> ORGANISM: Staphylococcus aureus

<400> SEQUENCE: 4
caattatcca accgggtg                                                 18

<210> SEQ ID NO 5
<211> LENGTH: 20
<212> TYPE: DNA
<213> ORGANISM: Staphylococcus aureus

<400> SEQUENCE: 5
tagtcatttt tcctgcataa                                               20

<210> SEQ ID NO 6
<211> LENGTH: 20
<212> TYPE: DNA
<213> ORGANISM: Staphylococcus aureus

<400> SEQUENCE: 6

-continued

```
tagtcatttt acctgcataa                                               20

<210> SEQ ID NO 7
<211> LENGTH: 17
<212> TYPE: DNA
<213> ORGANISM: Staphylococcus aureus

<400> SEQUENCE: 7
tgtaactttc tgggcct                                                  17

<210> SEQ ID NO 8
<211> LENGTH: 17
<212> TYPE: DNA
<213> ORGANISM: Staphylococcus aureus

<400> SEQUENCE: 8
tgtaactttc tggacct                                                  17

<210> SEQ ID NO 9
<211> LENGTH: 22
<212> TYPE: DNA
<213> ORGANISM: Artificial Sequence
<220> FEATURE:
<223> OTHER INFORMATION: 153_USA300_F

<400> SEQUENCE: 9
tcaatccttc acgcacgtta ac                                            22

<210> SEQ ID NO 10
<211> LENGTH: 18
<212> TYPE: DNA
<213> ORGANISM: Artificial Sequence
<220> FEATURE:
<223> OTHER INFORMATION: 153_USA300_R

<400> SEQUENCE: 10
gagcgcaggc agaaatcg                                                 18

<210> SEQ ID NO 11
<211> LENGTH: 20
<212> TYPE: DNA
<213> ORGANISM: Artificial Sequence
<220> FEATURE:
<223> OTHER INFORMATION: 153_USA300-A_FAM

<400> SEQUENCE: 11
ataataacat acgcttcatc                                               20

<210> SEQ ID NO 12
<211> LENGTH: 20
<212> TYPE: DNA
<213> ORGANISM: Artificial Sequence
<220> FEATURE:
<223> OTHER INFORMATION: 153_non300-C_VIC

<400> SEQUENCE: 12
aaataataac atccgcttca                                               20

<210> SEQ ID NO 13
<211> LENGTH: 23
<212> TYPE: DNA
<213> ORGANISM: Artificial Sequence
<220> FEATURE:
<223> OTHER INFORMATION: 106_USA300_F
```

```
<400> SEQUENCE: 13
agttgaactt gcagcacaac atg                                          23

<210> SEQ ID NO 14
<211> LENGTH: 24
<212> TYPE: DNA
<213> ORGANISM: Artificial Sequence
<220> FEATURE:
<223> OTHER INFORMATION: 106_USA300_R

<400> SEQUENCE: 14
cctgtgacta ccattgcaat acca                                         24

<210> SEQ ID NO 15
<211> LENGTH: 19
<212> TYPE: DNA
<213> ORGANISM: Artificial Sequence
<220> FEATURE:
<223> OTHER INFORMATION: 106_USA300-A_FAM

<400> SEQUENCE: 15
caattatcca accgagtgg                                               19

<210> SEQ ID NO 16
<211> LENGTH: 18
<212> TYPE: DNA
<213> ORGANISM: Artificial Sequence
<220> FEATURE:
<223> OTHER INFORMATION: 106_non300-C_VIC

<400> SEQUENCE: 16
caattatcca accgggtg                                                18

<210> SEQ ID NO 17
<211> LENGTH: 26
<212> TYPE: DNA
<213> ORGANISM: Artificial Sequence
<220> FEATURE:
<223> OTHER INFORMATION: 105_USA600_F

<400> SEQUENCE: 17
aaacaagagg caattcaaat aactca                                       26

<210> SEQ ID NO 18
<211> LENGTH: 27
<212> TYPE: DNA
<213> ORGANISM: Artificial Sequence
<220> FEATURE:
<223> OTHER INFORMATION: 105_USA600_R

<400> SEQUENCE: 18
ggtaccctat ttgcgacact attaact                                      27

<210> SEQ ID NO 19
<211> LENGTH: 20
<212> TYPE: DNA
<213> ORGANISM: Artificial Sequence
<220> FEATURE:
<223> OTHER INFORMATION: 105_USA600-T_FAM

<400> SEQUENCE: 19
tagtcatttt tcctgcataa                                              20

<210> SEQ ID NO 20
<211> LENGTH: 20
```

```
<212> TYPE: DNA
<213> ORGANISM: Artificial Sequence
<220> FEATURE:
<223> OTHER INFORMATION: 105_non600-A_VIC

<400> SEQUENCE: 20
tagtcatttt acctgcataa                                              20

<210> SEQ ID NO 21
<211> LENGTH: 23
<212> TYPE: DNA
<213> ORGANISM: Artificial Sequence
<220> FEATURE:
<223> OTHER INFORMATION: 259_USA100_F

<400> SEQUENCE: 21
tcgtaataac gatcactggc aat                                          23

<210> SEQ ID NO 22
<211> LENGTH: 25
<212> TYPE: DNA
<213> ORGANISM: Artificial Sequence
<220> FEATURE:
<223> OTHER INFORMATION: 259_USA100_R

<400> SEQUENCE: 22
ggctttcttt ctaactgcat tacca                                        25

<210> SEQ ID NO 23
<211> LENGTH: 17
<212> TYPE: DNA
<213> ORGANISM: Artificial Sequence
<220> FEATURE:
<223> OTHER INFORMATION: 259_USA100-G_FAM

<400> SEQUENCE: 23
tgtaactttc tgggcct                                                 17

<210> SEQ ID NO 24
<211> LENGTH: 19
<212> TYPE: DNA
<213> ORGANISM: Artificial Sequence
<220> FEATURE:
<223> OTHER INFORMATION: 259_non100-A_VIC

<400> SEQUENCE: 24
tgtaactttc tggacctgt                                               19
```